United States Patent
Abdalla et al.

(10) Patent No.: US 11,284,883 B2
(45) Date of Patent: Mar. 29, 2022

(54) MECHANICAL SUTURING DEVICE FOR AUTOMATED CLOSURE OF THE LINEA ALBA OF THE ABDOMINAL WALL POST MIDLINE LAPAROTOMY INCISION

(71) Applicant: HOSPITAL DAS CLINICAS DA FACULDADE DE MEDICINA DA UNIVERSIDADE DE SÃO PAULO—HCFMUSP, São Paulo (BR)

(72) Inventors: Ricardo Abdalla, São Paulo (BR); Helio Ozawa, São Paulo (BR)

(73) Assignee: HOSPITAL DAS CLINICAS DA FACULDADE DE MEDICINA DA UNIVERSIDADE DE SÃO PAULO-HCFMUSP, Sao Paulo (BR)

( * ) Notice: Subject to any disclaimer, the term of this patent is extended or adjusted under 35 U.S.C. 154(b) by 0 days.

(21) Appl. No.: 16/634,501

(22) PCT Filed: Aug. 11, 2017

(86) PCT No.: PCT/BR2017/050228
§ 371 (c)(1),
(2) Date: Jan. 27, 2020

(87) PCT Pub. No.: WO2019/018907
PCT Pub. Date: Jan. 31, 2019

(65) Prior Publication Data
US 2020/0229811 A1    Jul. 23, 2020

(30) Foreign Application Priority Data

Jul. 28, 2017    (BR) .......................... 102017016192-7

(51) Int. Cl.
*A61B 17/04*    (2006.01)
*A61B 17/32*    (2006.01)

(52) U.S. Cl.
CPC ...... *A61B 17/0487* (2013.01); *A61B 17/0482* (2013.01); *A61B 17/0483* (2013.01);
(Continued)

(58) Field of Classification Search
CPC . A61B 17/04; A61B 17/0469; A61B 17/0482; A61B 17/32; A61B 2017/00314;
(Continued)

(56) References Cited

U.S. PATENT DOCUMENTS

| | | | | |
|---|---|---|---|---|
| 5,954,731 A * | 9/1999 | Yoon | ..................... | A61B 17/062 606/144 |
| 6,224,614 B1 * | 5/2001 | Yoon | ..................... | A61B 17/062 606/147 |

(Continued)

FOREIGN PATENT DOCUMENTS

| | | |
|---|---|---|
| BR | PI0615841 | 5/2011 |
| WO | WO 2013/032329 | 3/2013 |
| WO | WO 2013/070841 | 5/2013 |

OTHER PUBLICATIONS

International Search Report for International (PCT) Patent Application No. PCT/BR2017/050228, dated Feb. 19, 2018, 4 pages.

*Primary Examiner* — George J Ulsh
(74) *Attorney, Agent, or Firm* — Sheridan Ross P.C.

(57) ABSTRACT

Surgical instruments for surgical suturing, for the purpose of enabling direct vision access, abdominal wall suturing and procedures of minimum invasion of abdominal structure from the surface thereof to deeper layers.

3 Claims, 8 Drawing Sheets

(52) U.S. Cl.
CPC ...... *A61B 17/32* (2013.01); *A61B 2017/0488* (2013.01); *A61B 2017/320044* (2013.01)

(58) Field of Classification Search
CPC .. A61B 2017/00327; A61B 2017/0488; A61B 2017/081; A61B 2017/320044; A61B 90/361
See application file for complete search history.

(56) References Cited

U.S. PATENT DOCUMENTS

| | | | | |
|---|---|---|---|---|
| 7,628,796 | B2 * | 12/2009 | Shelton, IV | A61B 1/00087 606/139 |
| 8,137,339 | B2 * | 3/2012 | Jinno | A61B 34/35 606/1 |
| 2009/0234379 | A1 | 9/2009 | Rehnke | |
| 2010/0100125 | A1 * | 4/2010 | Mahadevan | A61B 17/06066 606/223 |
| 2011/0313433 | A1 * | 12/2011 | Woodard, Jr. | A61B 17/062 606/145 |
| 2012/0123471 | A1 * | 5/2012 | Woodard, Jr. | A61B 17/06004 606/223 |
| 2012/0150199 | A1 * | 6/2012 | Woodard, Jr. | A61B 17/0469 606/147 |
| 2013/0282027 | A1 | 10/2013 | Woodard, Jr. et al. | |

\* cited by examiner

MECHANICAL SUTURING DEVICE FOR AUTOMATED CLOSURE OF THE LINEA ALBA OF THE ABDOMINAL WALL POST MIDLINE LAPAROTOMY INCISION

CROSS REFERENCE TO RELATED APPLICATIONS

This application is a national stage application under 35 U.S.C. 371 and claims the benefit of PCT Application No. PCT/BR2017/050228 having an international filing date of 11 Aug. 2017, which designated the United States, which PCT application claimed the benefit of Brazil Patent Application No. BR102017016192-7 filed 28 Jul. 2017, the disclosures of each of which are incorporated herein by reference in their entireties.

FIELD OF THE INVENTION

The present invention relates to a mechanical suturing device, belonging to the field of surgical instruments for surgical suturing. More particularly, the apparatus is intended for the automated closure of the linea alba of the abdominal wall post midline laparotomy incision, with the purpose of enabling direct vision access, abdominal wall suturing and procedures of minimum invasion of abdominal structures from the surface thereof to deeper layers.

This is a device that can be industrially produced, and is routinely used in any surgery service that deals with laparotomies, open surgeries, urgent surgeries, emergency surgeries or elective surgeries, in order to facilitate and decrease the time of use of the operating room and by stabilizing the closure in a systematic and standardized manner, thus reducing complications such as infection in the immediate postoperative period and possible new interventions for hernia repair in the late postoperative period.

DESCRIPTION OF THE PRIOR ART

The introduction of minimally invasive surgery has changed the way many operations have been performed. The benefits of using laparoscopy within the peritoneal cavity have quickly become evident. However, the use of this method on the abdominal wall has been delayed due to the lack of technological development and the need for a wider range of articulated movements, requiring more investment and time for its development {1, 2, 3}.

Laparoscopic treatment of abdominal wall weakness in cases of ventral and incisional hernia is widely used, with the use of synthetic mesh associated to this type of surgery revolutionizing this treatment {1, 2, 3}. Previously, the use of intra-peritoneal mesh was not considered adequate due to its characteristics and limitations. However, new engineering concepts have changed this scenario. Since a condition can manifest itself in many ways, there is no standard procedure, for this reason it depends on many predisposing and precipitating factors, with subjective and variable characteristics {4, 5}. The video surgery was first introduced in 1991 and was later used in several types of cases. Since 2000, there have been a series of comparisons and randomized controlled trials resulting published or discussed articles in dedicated sessions. Laparoscopic surgery has become a preferred treatment option for recurrent hernias and bariatric surgery, particularly for obese people {6, 7, 8}.

In published papers, the Rives-Stoppa technique is considered one of the preferred approaches for the open repair of incisional hernias {9, 10, 11}. Benefits include placing the sublay mesh along with abdominal closure, showing good results, with minor complications and low recurrence rates.

Obese patients treated with open surgery are known to have a 20% risk of incisional hernia [5]. A laparoscopic approach should be considered a good option for these patients because of obesity comorbidities and the benefits of video surgery.

Thus, taking into account the advantages of minimally invasive surgery, our operative technique to repair the abdominal wall was based on the principles of Rives-Stoppa {12} with the addition of new technical facilities and materials. The procedure was designed to reconstruct the median line of the peritoneal cavity, as a mirrored view of the abdominal wall, bringing the rectus abdominis muscles together and, at the same time, creating a posterior suture line with a retro-muscular space, where the mesh is implanted.

Methods

During a research performed by one of the inventors, patients with an incisional hernia developed after bariatric surgery were selected for surgeries. The size of the prosthesis was measured by taking the sublay space of the rectus abdominis muscle and maintaining 6 cm on each side of the repaired defect. The mesh was placed behind the rectus muscles, in front of the posterior sheaths. We used a polypropylene mesh in all cases. After positioning the mesh, we fixed the sheaths/posterior mesh against the rectus muscles with an intraperitoneal hernia stapler, along the midline on both sides. In this study, the aim was to evaluate the laparoscopic technique of midline reconstruction for the treatment of incisional hernia, located on the ventral supraumbilical, and to establish its feasibility, efficacy and morbidity.

Surgical Technique

The patient is placed in the supine position on the operating table, which is flexed concave in order to lower the legs.

This helps to avoid the obstruction of the optics and the limitation of the instrument's movement on the thighs during the procedure. Large abdominal exposure and the placement of a self-adhesive plastic curtain on the skin are performed. Antibiotic prophylaxis with second-generation cephalosporin is performed and a general anesthetic is administered. A Veress needle is introduced into the left subcostal anterior axillary line and a pneumoperitoneum is produced.

A 5 mm cannula is then introduced 2 cm below the left costal margin. A pressure of 12 mm of mercury is maintained and a complete exploration of the abdominal cavity is performed. Then, using 5 mm optics, a total of three laparoscopic cannulas are placed in a transverse line approximately 2 cm above the pubic symphysis. A 12 mm cannula is used in the midline, as it will eventually accommodate a linear stapler. On both sides, around the middle axillary line, 5 mm cannulas are placed.

Extensive adhesiolysis is performed, removing all adhesions to the anterior abdominal wall. Usually, the optics must be moved between the four cannulas and all adhesions are released with a scissors. Once all adhesions are removed and the defect is clearly delineated, the peritoneum and the sheaths of the posterior rectus are incised approximately 4 cm below the navel in a transverse direction for a distance of about 2 cm, on each side of the rectus muscle. A blunt dissector, a round-tipped laparoscopic instrument, is then introduced into one of the open sides (between the posterior rectus sheath and rectus muscle) and progressively moved cranially, quite lateral to the hernia defect until the costal margin is reached. The same procedure is then repeated on the opposite side.

The blades of a 12 mm laparoscopic linear cutter with 49 mm clips (green load) are then introduced into these tunnels located 4 cm below the navel. Since the hernia defect is always located above the navel, the stapler can be introduced through the previously created incisions, regardless of the size of the hernia, working as a zipper. It is fired, applying the sheaths of the posterior rectus in two lines, one anterior, the other posterior. The progressive movement staples and cuts the hernia sac, along with the posterior sheath, below the rectus muscles, while closing the defect and bringing the rectus abdominis muscles closer together. This approach is immediate, as is the closing of the defect. Several stapler loads are progressively fired cranially to the costal margin.

Like blades of a 12 mm linear cutter with 49 mm clamps (green load), they are then introduced into these tunnels located 4 cm below the navel. Since the inheritance defect is always above the navel, the stapler can be introduced through the previous incisions, regardless of the size of the hernia, working as a zipper. It is fired, applying sheaths to the posterior rectum in two lines, one anterior, one posterior. The progressive movement staples and cuts the hernia sac, along with the posterior sheath, below the rectus muscles, while closing the defect and bringing the rectus abdominis muscles closer together. This approach is immediate, as is the closing of the defect. Several stapler loads are progressively fired cranially to the costal margin.

Results

Blades of a 12 mm linear cutter with 49 mm clamps (green load) are then introduced into these tunnels located 4 cm below the navel. Since the inheritance defect is always above the navel, the stapler can be introduced through the incisions beforehand, working as a zipper. It is fired, applying sheaths to the posterior rectum in two lines, one anterior, one posterior. The progressive movement staples and cuts the hernia sac, along with the posterior sheath, below the rectus muscles, while closing the defect and bringing the rectus abdominis muscles closer together. This approach is immediate, as is the closing of the defect. Several stapler loads are progressively fired cranially to the costal margin.

The surgery was successfully performed in most cases through three ports; The average number of defects due to incisional hernias was 2 (1-4). According to Muysoms et al., (Hernia 2009) hernias were classified using the European Hernia Society classification for hernias of the incisional abdominal wall {24}. They were all midline, epigastric (M2) and/or umbilical (M3) hernias, recurrent or not, with an average width of 4.49 cm (2.1-9) and a length of 14 cm (7.5-20.5). The average surgery time was 114.3 min (90-170), and the median hospital stay was 1 day. Five patients (33%) used only standard paracetamol analgesia and 6 had opioids on the first day, for 1 day.

Considerations

The prevalence and incidence of incisional and ventral hernias are not insignificant, varying from 4.9 to 54% in some cases {4, 5}. It is also known that 35% of individuals who have an incisional hernia will have them again in the first year after the procedure. The level of recurrence after hernia repair is up to 40%; This reduced to 4% in the case of the Rives-Stoppa technique and 35-40% in other cases {13, 14}.

According to van Ramshorst et al., Who studied a cohort of an American population, the vast majority of patients with incisional hernia are symptomatic and have lower health-related quality of life in physical components and worse body image {15}.

The same study showed that the impact on obese patients is even worse. These patients have a higher incidence of incisional hernia due to physiological characteristics and high rates of infections at the incision site. In addition, hernias in obese patients, even when they lose weight, are less well tolerated compared to other patients {15}.

In 1993, Leblanc et al. Published a study of five cases of hernia repair by the laparoscopic approach {1}. Since then, several studies have demonstrated the feasibility of the technique and the benefits of minimally invasive surgery (MIS) in cases with intra-peritoneal mesh placement, with or without closing the defect, but the concept of the technique has remained unchanged {16, 17}. Other studies have demonstrated the potential complications of this type of approach, with seroma being one of the main complications occurring in 25% of patients {18}.

Although traditional laparoscopy brings the benefits of minimally invasive surgery, better results in terms of recurrence and abdominal wall function are found in the Rives-Stoppa open technique {19}. However, when we consider the QOL findings, we can see the great advantage in laparoscopic surgery compared to the open surgical treatment of these types of hernias {20, 21, 22, 23}.

Thus, we focused on the need to develop a technique that could combine the advantages and benefits of the traditional MIS approach with the standard open Rives-Stoppa procedure. This combined method can be used in patients with a defect located in the midline and above the navel (ventral hernia), as classified by the EHS classification {24}.

It was proposed to place the mesh in a sublay position, without closing the defect, and many other authors tried new techniques with interposition of the hernia sac or pre-peritoneal access {25, 26, 27}. However, none of them tried to approximate the Rives-Stoppa procedure using MIS, which was our goal.

Thus, we designed this procedure with immediate closure of the defects, the reconstruction of the midline and the placement of the prosthesis in a retro-muscular location, using new technologies that can help make the procedure safer, more viable and easier. We found good results in terms of hernia recurrence, QOL and results demonstrated by postoperative imaging.

Although our study includes only a limited number of patients, it demonstrates a new technique that is equal in effectiveness to the standard open procedure (Rives-Stoppa), while adding all the benefits of the minimally invasive technique. This is a first attempt, in our service, to change the approach to the repair of incisional hernia, especially in obese patients after bariatric surgery using retro-muscular mesh placement. However, further studies need to be done to examine in more detail the benefits and results of this approach, in these patients and with other types of patients or with the use of different materials.

As previously demonstrated, the technique was initially proposed by endoscopic surgical method with adaptation of endo staplers already existing in the market for the mechanical suturing of intestinal loops.

Several constructive dispositions applied to the endoscopic suturing, and ways of use, had been developed until then (ex: MU 8700808-4 U2, PI 0615841-2 A2, PI 0806172-6 A2, US20090234379, US20090234461), in an attempt to propose ways to internally suturing and, by analogy, mechanically suturing the linea alba of the abdominal wall post midline laparotomy incision, however, the method requires the application of a dedicated device that can avoid the difficulties of adapting an instrument unrelated to the tissue and the anatomy of the region.

OBJECTIVES OF THE INVENTION

The main objective of the present invention is to facilitate and expedite the closure of the open abdominal wall due to access to the cavity by any therapeutic operative indication and/or specialty, in which the integrity of the aponeurotic muscle layers remains.

BRIEF DESCRIPTION OF THE INVENTION

Through these and other diverse aspects and needs of the technical environment, and seeking to apply the experience acquired in the practice of robot-assisted video surgery, the inventor developed the present invention, devising a mechanical suturing device for automated closure of the linea alba da abdominal wall post midline laparotomy incision.

The device attempts to respect current surgical precepts, including the respect of the distance between the suture points and the non-aggression of the tissues by using a minimally invasive surgical method, with dissection under direct view of the deeper, retro-muscular layers together with the abdominal rectus musculature, in its aponeurotic case.

The developed innovation promotes the approach safely and quickly closing the cavity at the level of the aponeurotic tissue of the medial muscles of the ventral abdomen, respecting the principles and the approach of the tissues in an equitable and non-ischemic way, favoring the full healing of the surgical opening, including in cases of urgency, emergency or elective abdominal midline surgeries.

The device consists of two sets of working bodies, articulated, flexible to each other and tied together like a spine in sequence of these bodies. Two parallel sets are prepared in order to complete and create a fitting system, male and female, one side being loaded by the suture elements and the other side of the fitting mold allowing the release of the support element and stability of the suture.

The articulated working tubes are therefore like two lateral and parallel creases. Its most anterior portion is like a movable head, equipped with a central camera, with an optical cleaning system and a curved instrument in this anterior end of the blunt dissector action, like a Kelly-type blunt dissector instrument. This allows the introduction of the device on each side of the myo-aponeurotic case of the abdominal rectus muscle under direct view, through blunt progression to complete cranio-caudal insertion and the placement of the device in each right and left muscle case, introducing all articulated parts that are part of the device in this space.

In each articulated body, there is a working set that will load devices that allow suturing, i.e., a longitudinal niche on the internal side of the equipment, where a tubular device enters, passing in sequence through diamond-shaped folding structures, so that a steel cable, if activated, may move said diamond-shaped folding structures in the direction of opening (locking) or closing (release), fitting or disengaging the set of the tubular structure, remaining embedded on the same level and rendering movement indifferent, releasing the system that crossed the aponeurosis, during preparation for sewing and leaving the approach ready and stable.

Each diamond-shaped folding structure, when activated, will project to the contralateral by the change of position. In this situation, it is possible to join its parts, that is, the external part projected by the activation, and fix them by a small rivet, creating a tunneled line with the aponeurosis tissue between the two sides of the instrument, shaped to allow the passage of a tubular structure that contains the suture thread going through the aponeurosis.

Thus, the approach of the contralateral side completes a guide path, in a light "zig-zag" that, after the passage of the tube with the internal wire, fixes the two aponeuroses and allows the tubular structure to slide, which comes out of the system by stripping the suture in this channel. The removal movement of the diamond-shaped folding structures allows the system to make a % turn over the wire, releasing the device.

The other two rivets that are parallel are drilled to allow the steel cable to pass for the actuation command. In the proximal portion, there is an instrument channel for introducing the tubular structure that has a needle and a fishbone-like thread, which will make the suture. The needle comes externally through the working ostium, goes through the instrument channel to the cranial level of the instrument's spine, to proceed with and finalize the suture, in an ideal position, when the diamond-shape apexes, which are already in a rectified line, are approached and embedded. At the proximal end, the equipment continues externally as a hose and culminates in two rigid handles containing a valve and control system, activated by pneumatic force to trigger the device.

At the end of the articulated anterior portion, there is a final end for approaching and joining the two parallel and lateral parts, which join the two sides of the abdominal wall and bring stability to activate the device. The movable and metallic main part is suspended by an "L" shaped retractor, which, when making a fold between the articulated hoses, allows their approach and lateral fitting, in order to prepare the two niches for suturing. When fitted, these retractors cross and form a pantographic axis, with a lever that reduces the tension between the parts. Each side attached to the equipment is approached and when we approach the external "U" openings, consequently approaching the internal columns, we are ready for the next step.

Now, with the system activated and closed with a locking system, the aponeurotic tissue is crossed by suture threads (H) with fillets such as unidirectional valves 0.5 cm apart and with 1 cm of total lateral length, according to the disposition of the longitudinal niches. The last step is the suture clamp, where the suture needle with the latches is reversed when penetrating the working channel, penetrating the tissues to be approached, sliding inside a rail where it is accommodated, in a smooth tube, which takes the thread toward and against the front part with a metallic needle, punctures the fabric and penetrates to the opposite level, on the side that is already being seen by the camera.

Being in the correct position, undoing the movement of the steel cable and retracting the diamond-shaped folding structures within the longitudinal niches, the set can be removed together with the tubular structure that allowed the suture to slide, which opens the splinters of the thread and it locks the tissue to be sutured, closing the portion of the abdominal wall involved in one movement, with the next steps involving cutting thread and repeating sequentially from the last point until closing the entire cavity.

Thus, the present patent was designed to obtain a device conveniently configured and arranged to allow the invention to be adopted in any surgery of the abdomen, without specialty restriction and being seen as a facilitator, expediting the closing of the wall with large incisions. It is applicable to widely irrigated tissues and should reduce local causes for infection and complications such as rupture of the aponeurosis, as it provides for an equal distribution of tension forces during the activation of the device.

BRIEF DESCRIPTION OF THE DRAWINGS

The object of this constructive provision will be explained in detail, with the help of the attached figures, where.

It should be noted that these figures are merely representative and may vary, as long as they do not deviate from what was initially required.

DETAILED DESCRIPTION OF THE INVENTION

In accordance with what the above figures illustrate, the "MECHANICAL SUTURING DEVICE FOR AUTOMATED CLOSURE OF THE LINEA ALBA OF THE ABDOMINAL WALL POST MIDLINE LAPAROTOMY INCISION", object of this patent, essentially comprising two working sets (1a) and (1b) parallel to each other, and made up of several vertebrae (2a) and (2b) joined sequentially by means of joints (3a) and (3b), forming flexible structures.

Figure 1:
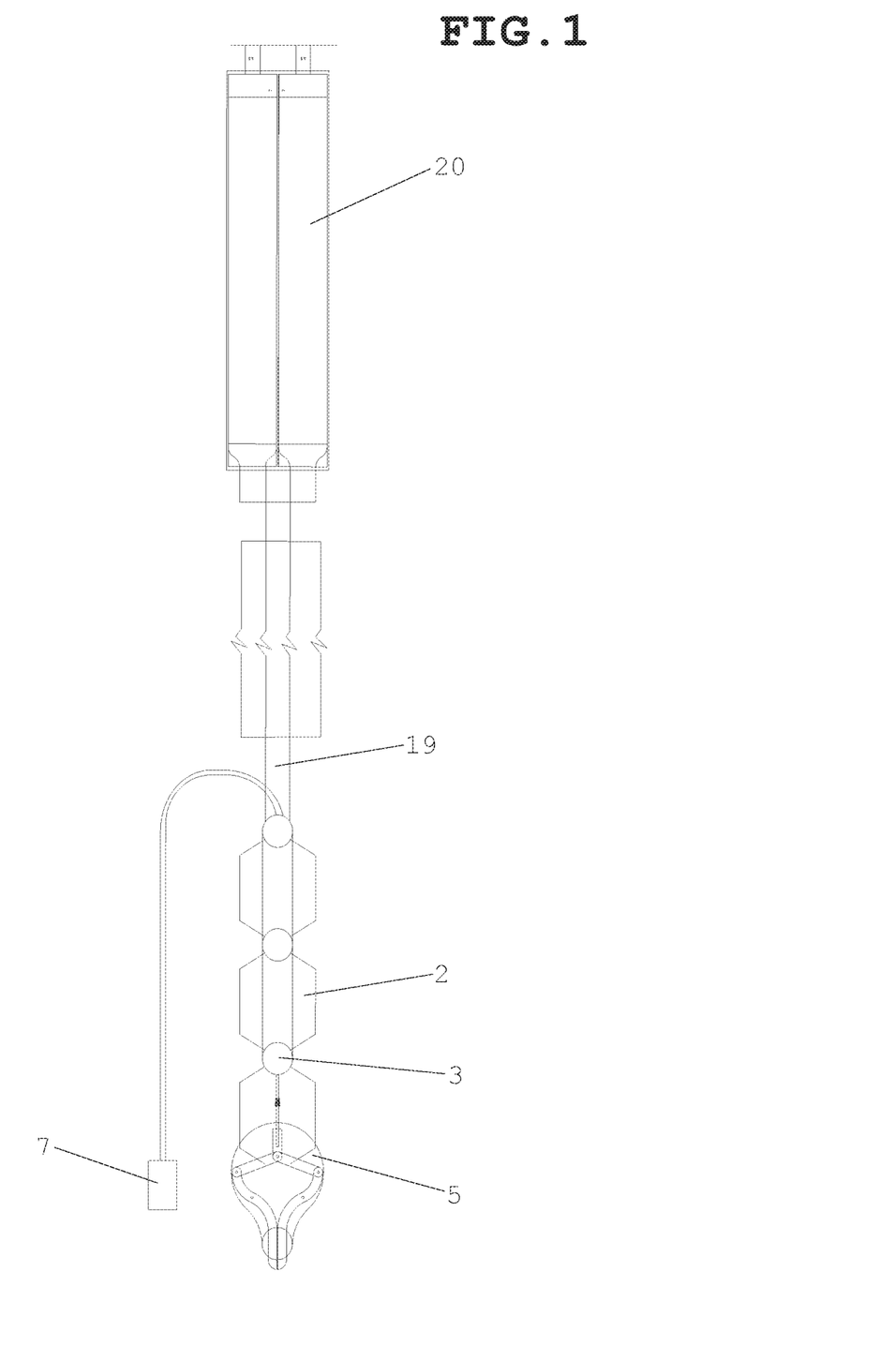
FIG. 1—Shows a side view of one of the articulated working bodies, an integral part of the mechanical suture device for automated closure of the abdominal wall linea alba after an incision by median laparotomy, which is the object of the present invention, illustrating its vertebrae sequentially united through joints, forming flexible structures.

Each set of articulated working bodies (1a) and (1b) bears central internal channels through which one or more cables (4a) and (4b) travel along with a linear movement device frontally equipped with a movable head (5a) and (5b) with blunt dissector action, with an internal central camera with an optical cleaning system (6a) and (6b), while later equipped with ducts with heads (7a) and (7b) that can be joined together in a parallel or crossed shape by a male and female fitting system, and allowing the release of the suture support and stability element, from the external side of the surgery. As an embodiment, such a blunt dissecting instrument can be a Kelly dissector or similar.

Figure 2:
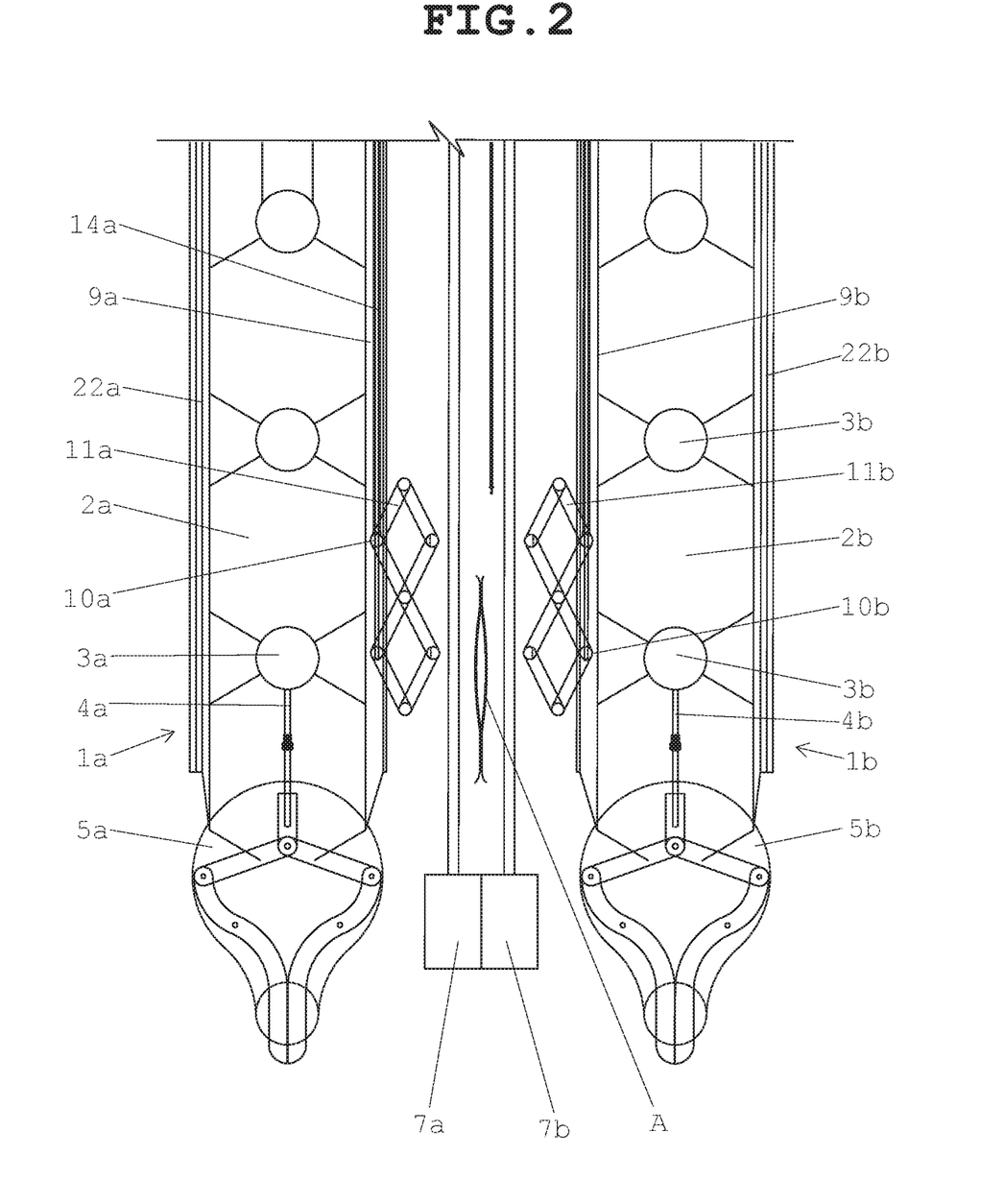
FIG. 2—Shows a top view of the working sets positioned around the aponeurosis, illustrating the working sets, and containing the flexible polymer sleeves with longitudinal channeled guides, whose openings face each other, and within which the respective pivoting eyelets contained at the ends of diamond-shaped folding structures, which are also transverse and centrally traversed by respective threaded bodies attached to drive cables arranged within the respective conduits, which in turn are arranged within the respective longitudinal channeled guides, while being controlled by linear and rotational motion devices.
Figure 8:
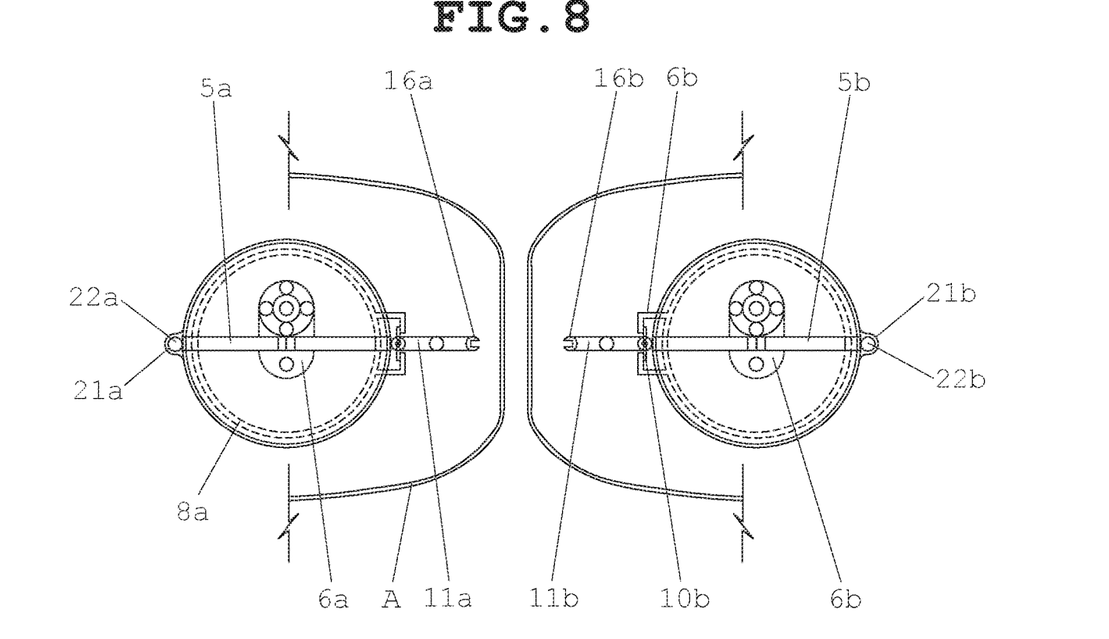
FIG. 8—Shows a front view of the working sets positioned around the aponeurosis, illustrating the working sets, and containing the flexible polymer sleeves with longitudinal channel guides, within which the respective pivoting eyelets contained at the ends of the diamond-shaped folding structures are attached in an extended position.

Flexible polymer sleeves (8a) and (8b) are arranged around each of the working sets (1a) and (1b), provided with longitudinal channeled guides (9a) and (9b), with openings facing one another, and within which the respective pivoting eyelets are attached (10a) or (10b) contained in the ends of diamond-shaped folding structures (11a) and (11b), which are also transversally and centrally crossed by respective threaded bodies (13a) or (13b) attached to drive cables arranged within the respective conduits (14a) or (14b), in turn arranged within the respective longitudinal channeled guides (9a), while being controlled by linear and rotational movement devices. Said diamond-shaped folding structures (11a) and (11b) present several free eyelets (15a) and (15b) equipped with "U" openings (16a) and (16b).

Figure 3:
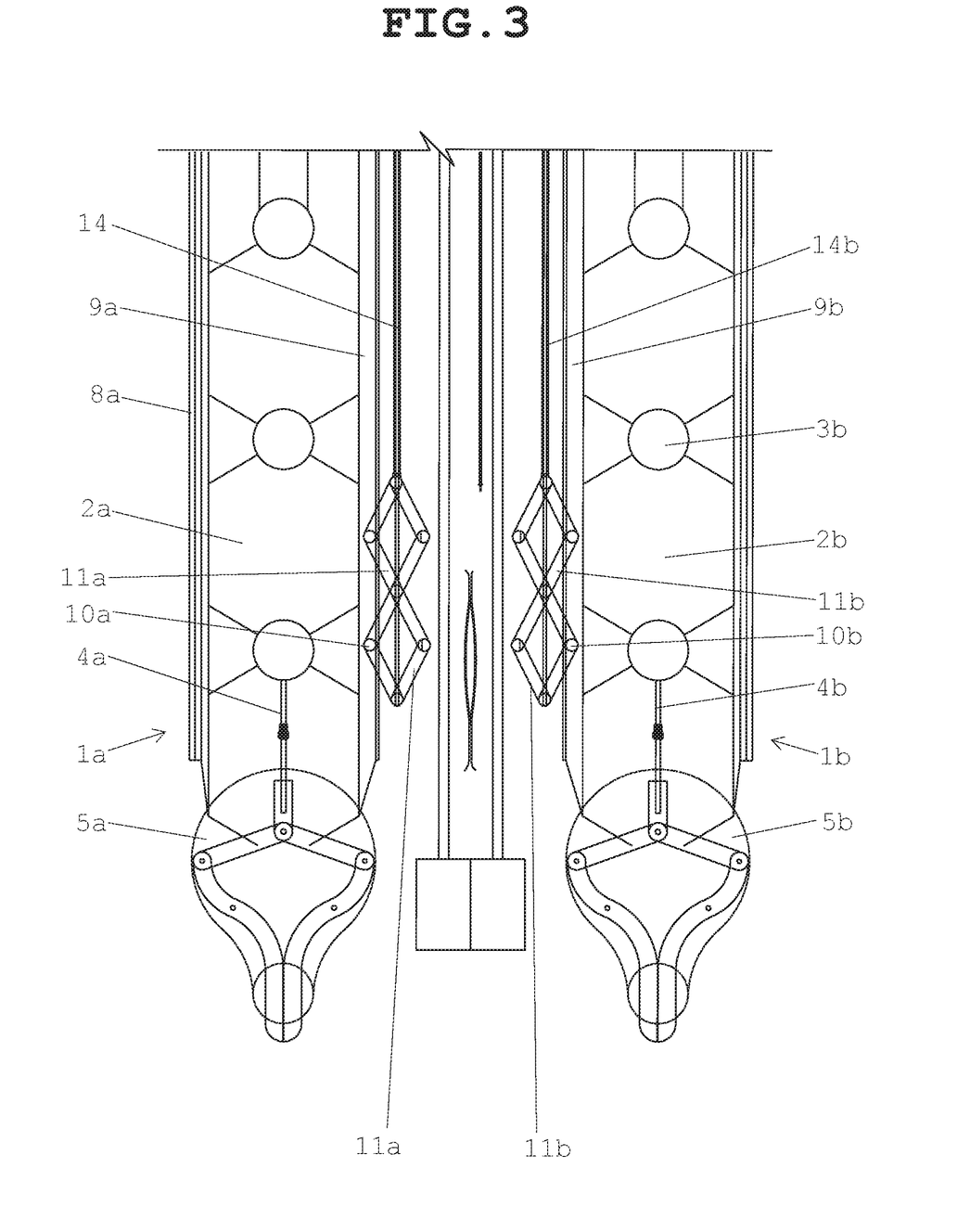
FIG. 3—Shows a top view of the working sets positioned around the aponeurosis, illustrating the embodiment where the central eyelets of the diamond-shaped folding structures are centrally passed through respective threaded bodies along the drive cables arranged within the respective conduits, in turn controlled by linear and rotational movement devices.
Figure 5:
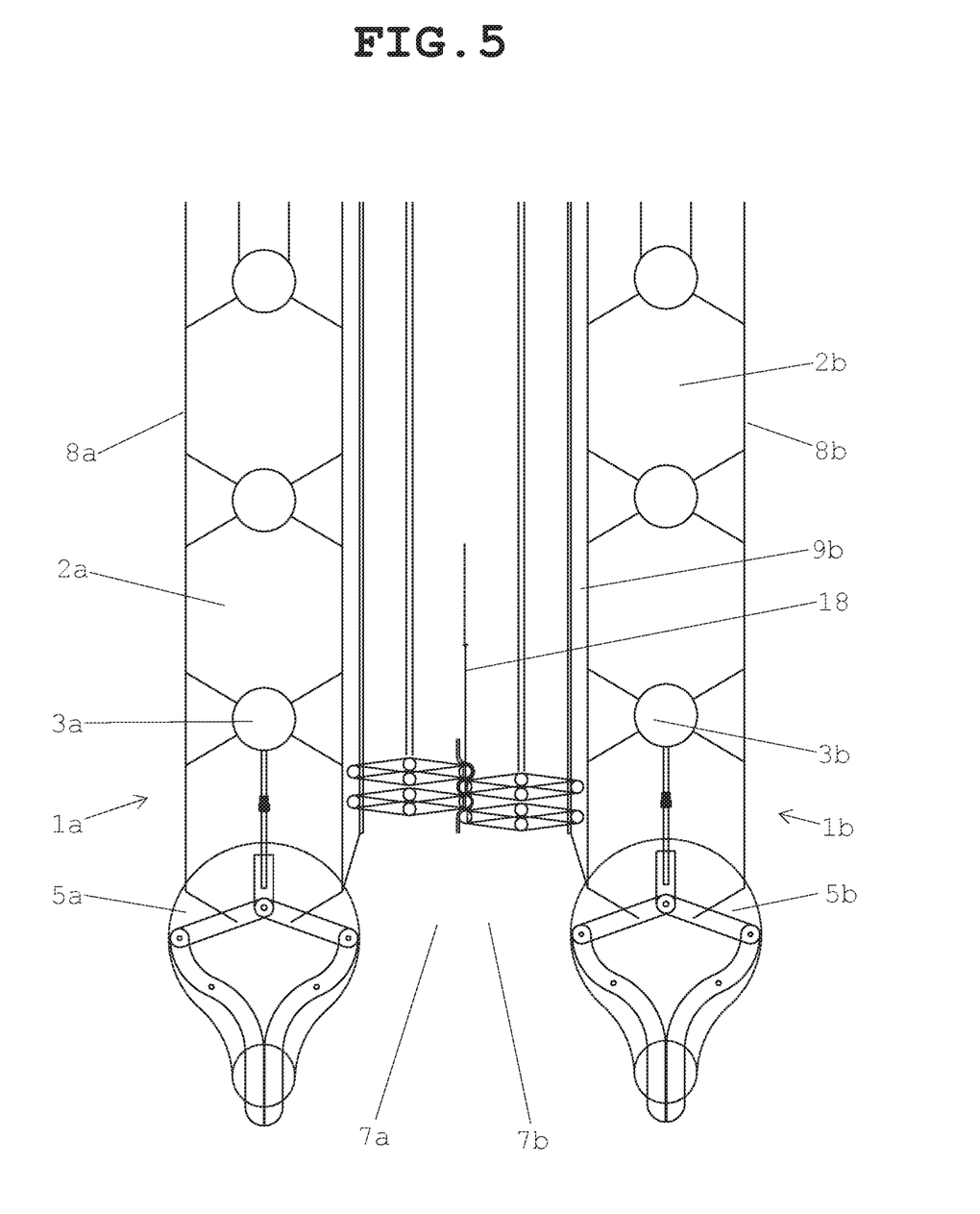
FIG. 5—Shows a top view of the working sets positioned around the aponeurosis, illustrating the modification where the threaded bodies are arranged through the central eyelets of the diamond-shaped structures. The locking effect of the aponeurosis is similar to that of FIG. 4.
Figure 6:
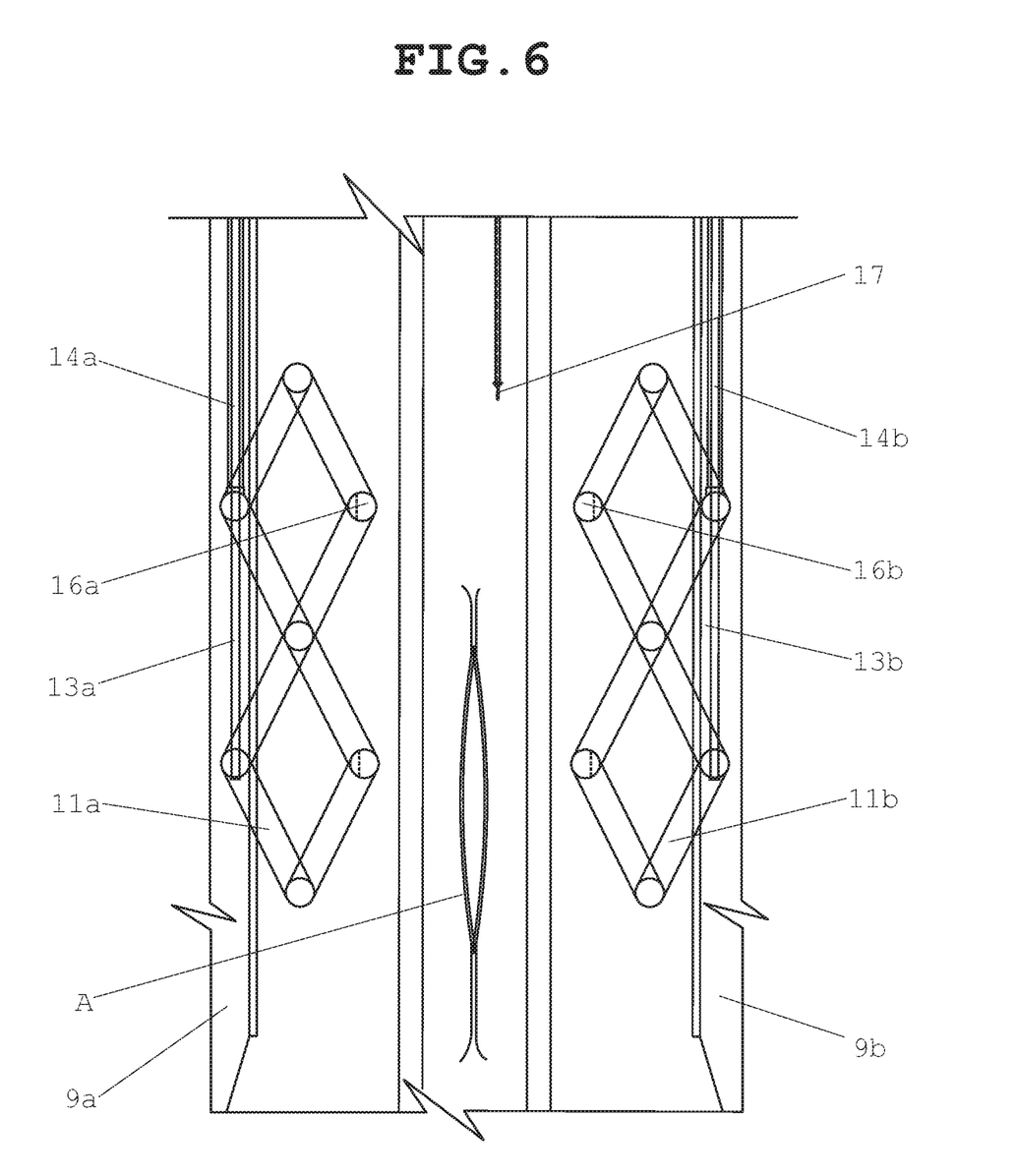
FIG. 6—Shows a top and partial view of FIG. 2, illustrating in more detail the extended diamond-shaped folding structures.

As another embodiment, the central eyelets (12a) or (12b) of the diamond-shaped folding structures (11a) and (11b) are centrally passed through the respective threaded bodies (13a) or (13b) along with drive cables arranged inside the respective conduits (14a) or (14b), in turn controlled by linear and rotational movement devices.

Both flexible polymer sleeves (8a) and (8b) are also endowed with longitudinal elevations (21a) and (21b), which have tunnels (22a) and (22b), inside which rigid rods are introduced which enter externally through the working ostium, able to assist the alignment and structuring of the working sets (1a) and (1b).

Figure 4:
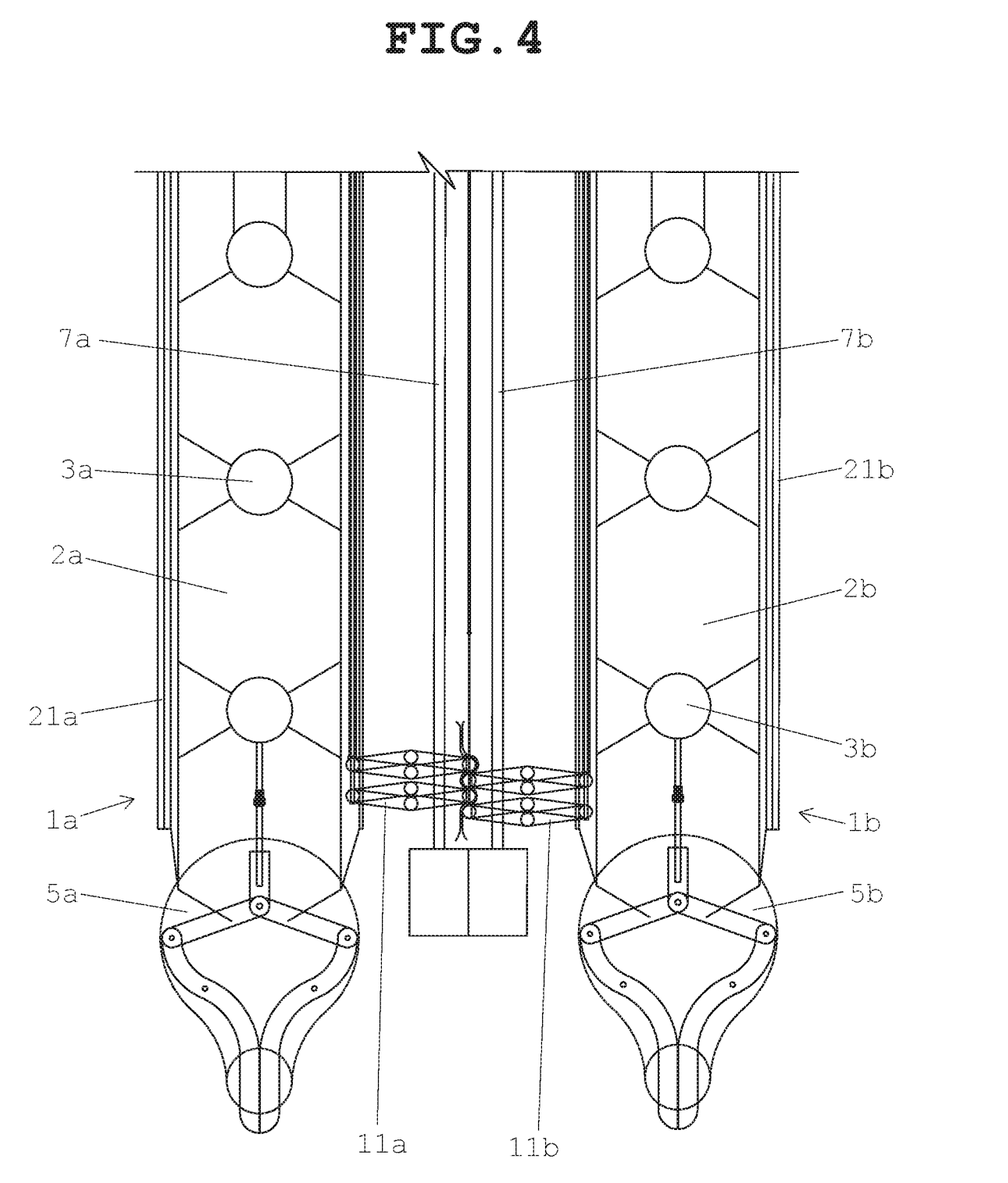
FIG. 4—Shows a top view of the working sets positioned around the aponeurosis, illustrating the working sets, and containing the flexible polymer sleeves with longitudinal channel guides, within which the respective pivoting eyelets contained at the ends of the folding diamond-shaped structures are attached in a locking and closing position of the aponeurosis by means of length reduction and transverse increase, by the action of the threaded bodies in the pivoting eyelets.
Figure 9:
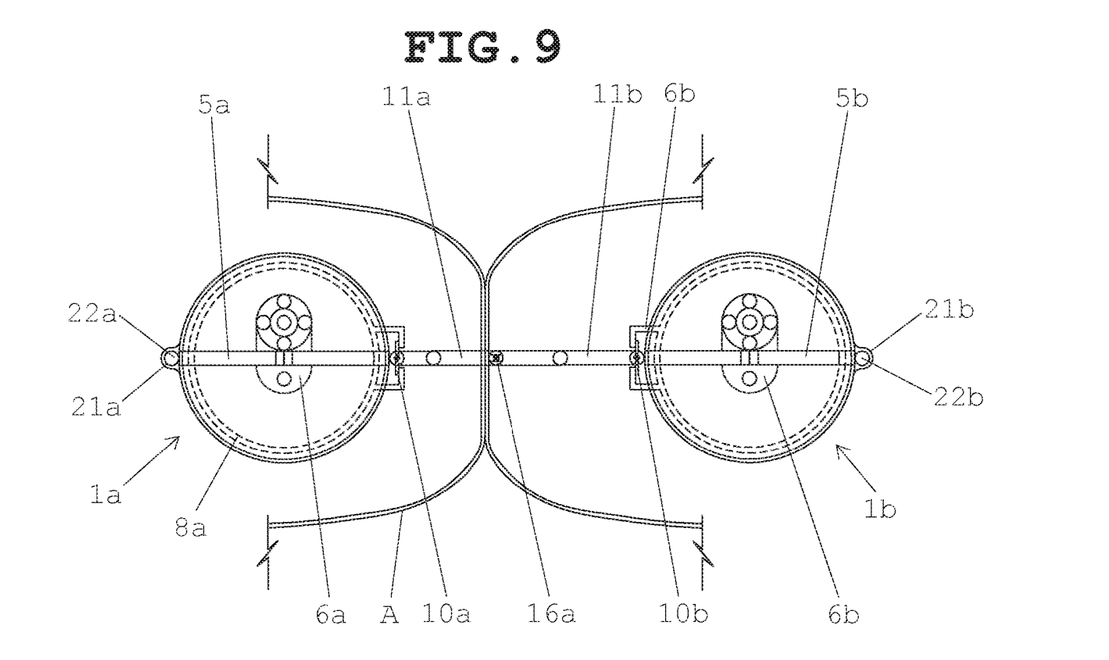
FIG. 9—Shows a front view of the working sets positioned around the aponeurosis, illustrating the working sets, and containing the flexible polymer sleeves with longitudinal channel guides, within which the respective pivoting eyelets contained at the ends of the folding diamond-shaped structures are attached in a locking and closing position of the aponeurosis by means of length reduction and transverse increase, by the action of the threaded bodies in said pivoting eyelets.

In this way, if the drive cables are rotated by a rotational movement device, they can: reduce the length of the diamond-shaped folding structures (11a) or (11b), increasing it transversely, stopping the movement of the system and;

increase the length of the diamond-shaped folding structures (11a) or (11b), reducing it transversely, releasing the movement of the system.

Figure 7:
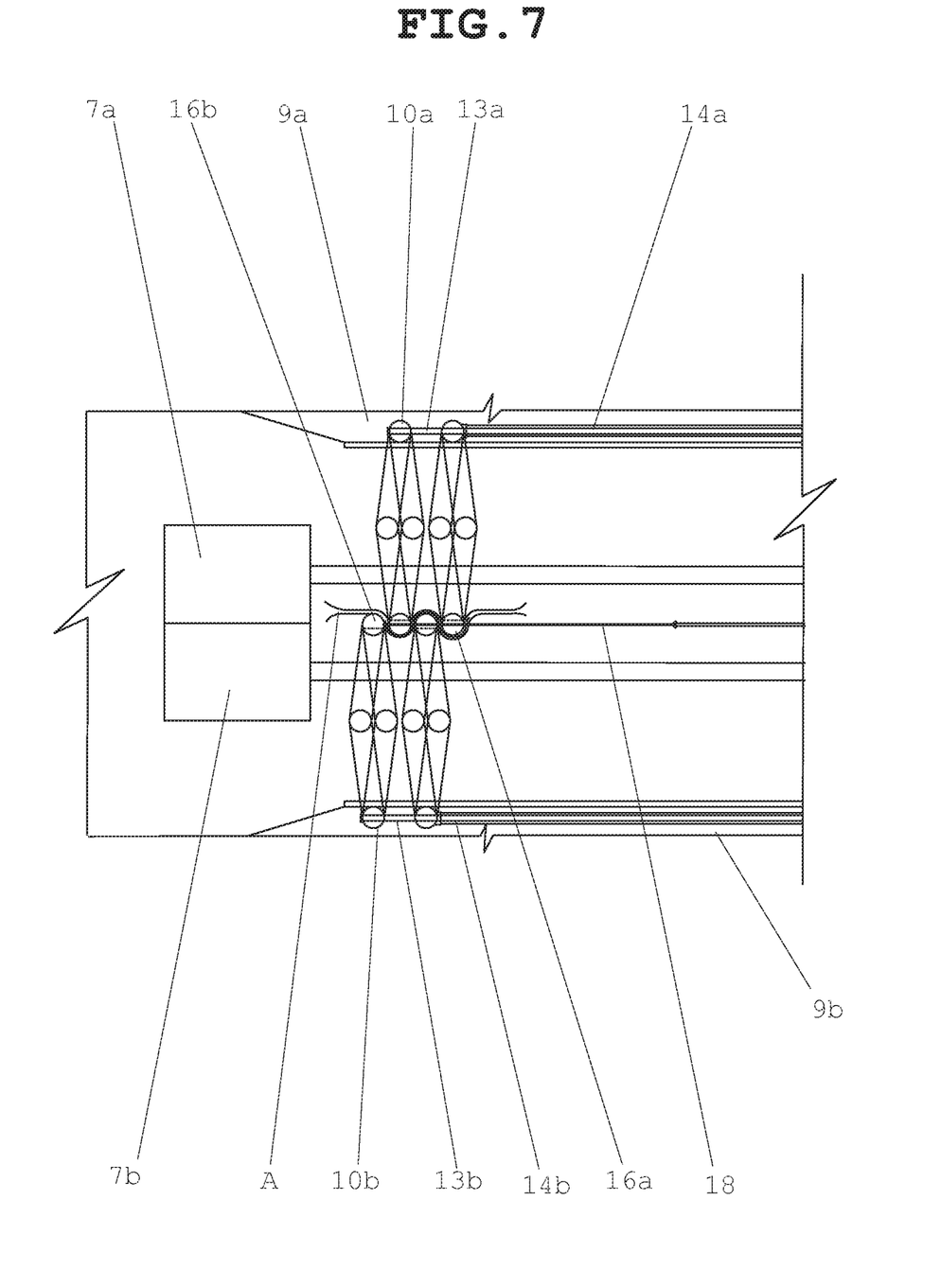
FIG. 7—Shows a top and partial view of FIG. 4, illustrating in more detail the diamond-shaped folding structures holding the aponeurosis by fitting it together in a slight "zig-zag" when misaligned by changing the linear position, making it possible to join the semipart parts of the aponeurosis and creating a tunneled line with the aponeurosis tissue between the various free eyelets provided with "U" openings arranged at the free ends of the respective diamond-shaped folding structures.

Both diamond-shaped folding structures (11a) or (11b), when activated, will project against each other, in order to fit together in a slight "zig-zag" when misaligned by a linear position change, making it possible to join the semi-parts of the aponeurosis (A) and creating a tunneled line with the aponeurosis tissue (A) between the various free eyelets (15a) and (15b) with "U" openings (16a) and (16b) arranged at the free ends of the respective diamond-shaped folding structures (11a) or (11b), and which allow the passage of a needle (17) with a suture thread (18), like a fish bone, which comes externally through the working ostium, follows in the direction of the "channel" formed by the "U" openings (16a) and (16b), to perforate, continue and finish the suture, in an ideal position, when approaching and inlaying the apexes of the diamond-shaped folding structures (11a) or (11b), which are already in a rectified line. After fixing the end of the suture thread (18), it is stripped, so that the two aponeuroses can be attached (A). After said movement, both threaded bodies (13a) or (13b) are actuated by the conduit activation cables (14a) or (14b), releasing the recoil movement of the diamond-shaped folding structures (11a) or (11b), releasing the working sets (1a) and (1b).

At the proximal end, each articulated working body (1a) or (1b) continues externally in the form of a hose (19) that culminates in solid handpieces (20) containing a valve and control system, activated by pneumatic force to trigger the devices.

Thus, one may notice that the "MECHANICAL SUTURING DEVICE FOR AUTOMATED CLOSURE OF THE LINEA ALBA OF THE ABDOMINAL WALL POST MIDLINE LAPAROTOMY INCISION" is very useful, presenting all the practical and functional qualities that fully justify the patent application for Privilege of Invention.

While the present request has been described with reference to the embodiment above, it will be apparent to those skilled in the art that other changes in the composition and process details can be made here, without departing from the spirit and scope of what is requested, as defined in the claims attached.

REFERENCES

{1} LeBlanc K A, Booth W V (1993) Laparoscopic repair of incisional abdominal hernias using expanded polytetrafluoroethylene: preliminary findings. Surg Laparosc Endosc 3:39-41.

{2} Moreau P E, Helmy N, Vons C (2012) Laparoscopic treatment of incisional hernia. Prior art in 2012. J Visc Surg 149(5 Suppl):e40-e48.

{3} Cuccurullo D, Piccoli M, Agresta F, Magnone S, Corcione F, Stancanelli V, Melotti G (2013) Laparoscopic ventral incisional hernia repair: evidence-based guidelines of the first Italian Consensus Conference. Hernia 17:557-566

{4} Mudge M, Hughes L E (1985) Incisional hernia: a 10 year prospective study of incidence and attitudes. Br J Surg 72:70-71.

{5} Nhoa R L H, Megea D, Ouaïssia M, Sieleznefffa I, Sastrea B (2012) Incidence and prevention of ventral incisional hernia. J Visc Surg 149:e3-e14.

{6} Bittner R, Bingener-Casey J, Dietz U, Fabian M, Ferzli G S, Fortelny R H, Köckerling F, Kukleta J, LeBlanc K, Lomanto D, Misra M C, Bansal V K, Morales-Conde S, Ramshaw B, Reinpold W, Rim S, Rohr M, Schrittwieser R, Simon Th, Smietanski M, Stechemesser B, Timoney M, Chowbey P (2014) Guidelines for laparoscopic treatment of ventral and incisional abdominal wall hernias (International Endohernia Society (IEHS)-part 1. Surg Endosc 28:2-29.

{7} Heniford B T, Park A, Ramshaw B J, Voeller G (2000) Laparoscopic ventral and incisional hernia repair in 407 patients. J Am Coll Surg 190:645-650.

{8} Hussain D, Sarfraz S L, Kasmani J A, Baliga K S, Ibrahim M, Syed H S, Aziz Z A, Hartung R U (2012) Laparoscopic repair of ventral hernia. J Coll Physicians Surg Pak 22(11):683-685. doi:11.2012/JCPSP.683685.

{9} Forte A, Zullino A, Manfredelli S, Montalto G, Covotta F, Pastore P, Bezzi M (2011) Rives technique is the gold standard for incisional hernioplasty. An institutional experience. Ann Ital Chir 82(4):313-317.

{10} Iqbal W, Pham T H, Joseph A, Thompson JMGB, Sarr M G (2007) Long-term outcome of 254 complex incisional hernia repairs using the modified Rives-Stoppa technique. World J Surg 31:2398-2404.

{11} Notash A Y, Notash A Y Jr, Farshi J S, Amoli H A, Salimi J, Mamarabadi M (2007) Outcomes of the Rives-Stoppa technique in incisional hernia repair: ten years of experience. Hernia 11:25-29

{12} Bauer J, Harris M, Gorfine S, Kreel I (2002) Rives-Stoppa procedure for repair of large incisional hernias: experience with 57 patients. Hernia 6(3):120-123.

{13} Wormer B A, Walters A L, Bradley J F, Williams K B, Tsirline V B, Augenstein V A, Heniford B T (2013) Does ventral hernia defect length, width, or area predict postoperative quality of life? Answers from a prospective, international study. J Surg Res 184:169-177.

{14} Burger J W, Lange J F, Halm J A, Kleinrensink G J, Jeekel H (2005) Incisional hernia: early complication of abdominal surgery. World J Surg 29:1608-1613.

{15} van Ramshorst G H, Eker H H, Hop W C J, Jeekel J, Lange J F (2012) Impact of incisional hernia on health-related quality of life and body image: a prospective cohort study. Am J Surg 204:144-150.

{16} Tse G H, Stutchfield B M, Duckworth A D, de Beaux A C, Tulloh B (2010) Pseudo-recurrence following laparoscopic ventral and incisional hernia repair. Hernia 14:583-587.

{17} Sasse K C, Lim D C L, Brandt J (2012) Long-term durability and comfort of laparoscopic ventral hernia repair. JSLS 16:380-386.

{18} Perrone J M, Soper N J, Eagon J C, Klingensmith M E, Aft R L, Frisella M M, Brunt L M (2005) Perioperative outcomes and complications of laparoscopic ventral hernia repair. Surgery 138:708-716.

{19} Williams R F, Martin D F, Mulrooney M T, Voeller G R (2008) Intraperitoneal modification of the Rives-Stoppa repair for large incisional hernias. Hernia 12:141-145.

{20} Stipa F, Giaccaglia V, Burza A, Santini E, Bascone B, Picchio M (2013) Incisional hernia: laparoscopic or open repair? Surg Laparosc Endosc Percutan Tech 23(4):419-422.

{21} Ji Y, Zhan X, Wang Y, Zhu J (2013) Combined laparoscopic and open technique for the repair of large complicated incisional hernias. Surg Endosc 27:1778-1783.

{22} Salvilla S A, Thusu S, Panesar S S (2012) Analysing the benefits of laparoscopic hernia repair compared to open repair: a meta-analysis of observational studies. J Minim Access Surg 8(4):111-117.

{23} Colavita P D, Tsirline V B, Belyansky I, Walters A L, Lincourt A E, Sing R F, Heniford B T (2012) Prospective, long-term comparison of quality of life in laparoscopic versus open ventral hernia repair. Ann Surg 256(5):714-722.

{24} Muysoms F E, Miserez M, Berrevoet F, Campanelli G, Champault G G, Chelala E, Dietz U A, Eker H H, El Nakadi I, Hauter P, Hidalgo Pascual M, Hoeferlin A, Klinge U, Montgomery A, Simmermacher R K J, Simons M P, Śmietański M, Sommeling C, Tollens T, Vierendeels T, Kingsnorth A (2009) Classification of primary and incisional abdominal wall hernias. Hernia 13:407-414.

{25} Schroeder A D, Debus E S, Schroeder M, Reinpold W M (2012) Laparoscopic transperitoneal sublay mesh repair: a new technique for the cure of ventral and incisional hernias. Surg Endosc 27(2):648-654.

{26} Prasad P, Tantia O, Patle N M, Khanna S, Sen B (2011) Laparoscopic transabdominal preperitoneal repair of ventral hernia: a step towards physiological repair. Indian J Surg 73(6):403-408.

{27} Hasbahcec M, Basak F (2013) Interposition of the hernia sac as a protective layer in repair of giant incisional hernia with polypropylene mesh. Surg Today 44(2):227-232.

{28} Abdalla R Z, Garcia R B, da Costa R I D, Abdalla B M Z (2013) Treatment of mid-line abdominal wall hernias with the use of endo-stapler for mid-line closure ABCD. Arq Bras Cir Dig 26(4):335-337.

What is claimed is:

1. A mechanical suturing device for automated closure of the linea alba of the abdominal wall post midline laparotomy incision, consisting of two working sets parallel to each other, and consisting of several vertebrae sequentially joined together by means of joints, forming flexible structures, the device having a proximal end external to the abdomen wall and a distal end configured to be positioned inside the abdomen;
   each working set of articulated working bodies presenting internal channels through which one or more cables travel along with diamond-shaped folding structures while frontally being equipped with a movable head with blunt dissector action, which internally has a central camera with an optical cleaning system;
   each set of articulated working bodies is characterized by being equipped with ducts equipped with heads that can be joined in parallel or crossed by a plug-in system, male and female, and allowing the release of a suture support and stability element from a location external to the abdominal wall;
   flexible polymer sleeves are arranged around each of the working sets, provided with longitudinal channel guides, with openings facing one another, and within which are diamond-shaped folding structures each having at least one pivoting eyelet, which are also transversally and centrally crossed by respective threaded bodies attached to drive cables, each threaded body arranged within a conduit, and each conduit arranged within the respective longitudinal channel guide, while being controlled by the drive cables;
   said diamond-shaped folding structures have several free eyelets equipped with "U" openings;
   both flexible polymeric sleeves are also endowed with longitudinal elevations, which have internal tunnels, inside which are rigid rods configured to be introduced externally through an opening in the abdomen;
   at the proximal end, each working set of articulated working bodies continues externally of the abdomen in the form of a hose which culminates in rigid handles.

2. The mechanical suturing device for automated closure of the linea alba of the abdominal wall post midline laparotomy incision according to claim 1, comprising central eyelets associated with the diamond-shaped folding structures, wherein the central eyelets are centrally passed through the respective threaded bodies attached to the drive cables arranged inside the respective conduits, while being controlled by the drive cables.

3. The mechanical suturing device for automated closure of the linea alba of the abdominal wall post midline laparotomy incision, according to claim 1,
   wherein each diamond-like structure comprises four segments joined at four apexes to form a diamond-like shape;
   wherein rotating the drive cables in a first direction reduces the length of the diamond-shaped folding structures, increasing it transversely, and stopping movement of the distal end of the device; and rotating the drive cables in a second direction increases the length of the diamond-shaped folding structures, reducing it transversely and releasing the movement of the distal end of the device;
   both diamond-shaped folding structures, when activated, will project against each other, in order to fit together in a slight "zig-zag" when misaligned by a linear position change, configure both the diamond-shaped folding structures to join the semi-parts of the aponeurosis and creating a tunneled line with the aponeurosis tissue between the various free eyelets with "U" openings and arranged at free ends of the respective diamond-shaped folding structures, and which allow the passage of a needle with a suture thread, which comes externally through the working ostium, follows in the direction of a channel formed by the "U" openings, to perforate, continue and finish forming a suture having an end, when approaching and inlaying adjacently located apexes of the diamond-shaped folding structures, which are already in a rectified line;
   after the end of the suture is fixed, it is stripped, so that the two aponeuroses can be fixed;
   after said movement, both threaded bodies are driven by the drive cables of the conduits, releasing the diamond-shaped folding structures, releasing the work sets.

* * * * *